United States Patent [19]
LeBlanc

[11] Patent Number: 5,257,439
[45] Date of Patent: Nov. 2, 1993

[54] QUICK RELEASE ADJUSTABLE DENTAL BAND CLAMP

[76] Inventor: Lester A. LeBlanc, 274 First Ave. #11F, New York, N.Y. 10009

[21] Appl. No.: 881,346

[22] Filed: May 11, 1992

[51] Int. Cl.⁵ ............................................. B65D 63/00
[52] U.S. Cl. .................................. 24/269; 24/274 R; 24/279
[58] Field of Search ..................... 24/274 R, 279, 280, 24/281, 269, 270; 433/3, 23

[56] References Cited

U.S. PATENT DOCUMENTS

| | | | |
|---|---|---|---|
| 2,383,199 | 8/1945 | Kitts | 24/269 |
| 2,384,094 | 9/1945 | Jamie | 24/274 R |
| 2,750,645 | 6/1956 | Seltzer | 24/279 |
| 2,917,621 | 12/1959 | Higgins | 24/280 |
| 4,283,816 | 8/1981 | Tanaka | 24/269 |
| 4,604,773 | 8/1986 | Weber et al. | 24/269 |
| 4,972,558 | 11/1990 | Maid et al. | 24/274 R |

FOREIGN PATENT DOCUMENTS 1256422  2/1961  France ................ 24/274 R

Primary Examiner—Victor N. Sakran

[57] ABSTRACT

A Quick Release Adjustable Dental Band Clamp is intended to rigidly fix orthodontic attachments to a tooth. There are two major advantages to this invention. First, the band clamp can be compressed to a near-size fit by finger pressure, thereby, reducing operator time with the hand tool. Second, the clamp provides a quick release of tension, enabling fast removal. The clamp is a flexible metal strip with two free ends. One end contains a permanently fixed joining mechanism which is the heart of the invention. The other end is designed to be pulled by a joining mechanism into a created holes interior. The joining mechanism has two main operative parts: a worm and a locking pin. The worm draws the band material tightly and is governed by the locking pin, which is either engaged or disengaged with worm. When the locking pin is engaged with the worm only tightening is permitted. Loosening is allowed when the locking pin is disengaged.

6 Claims, 2 Drawing Sheets

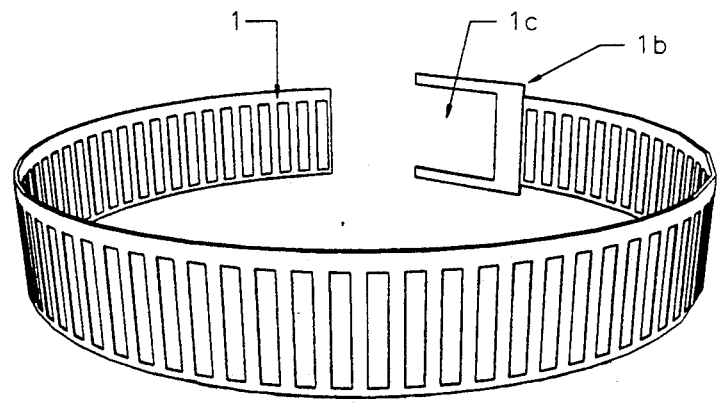
figure 4
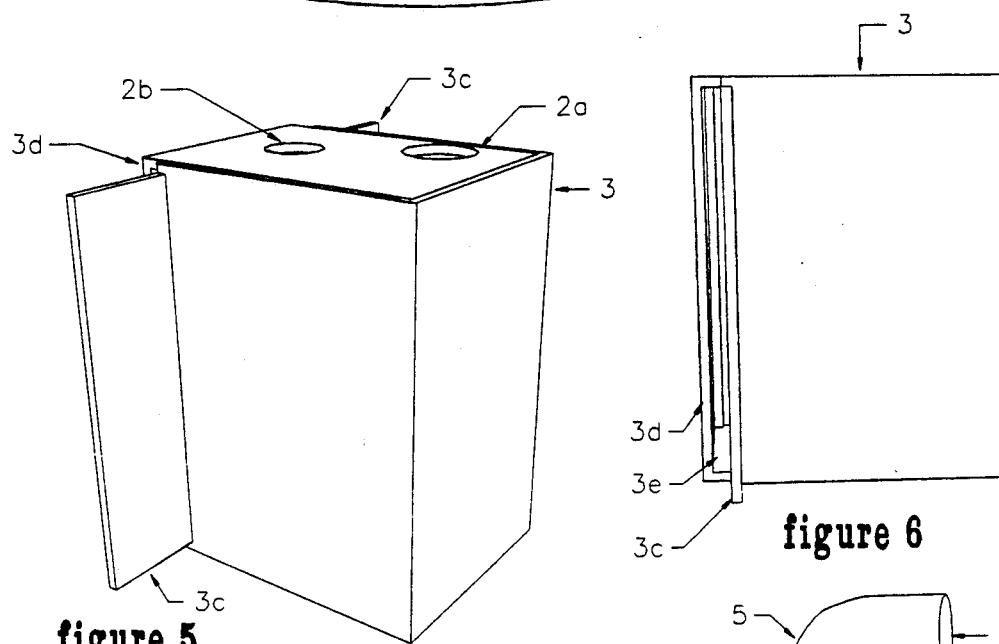
figure 5
figure 6
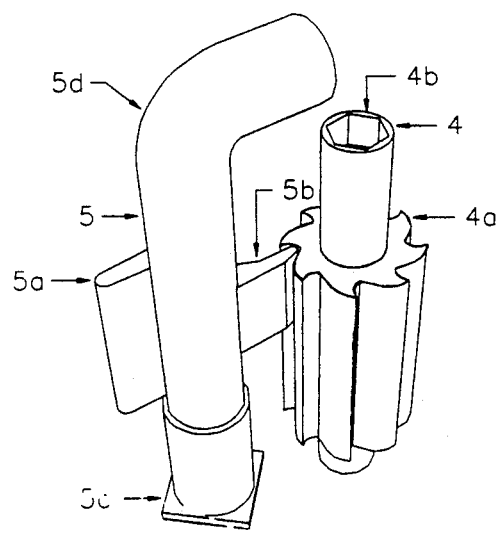
figure 7
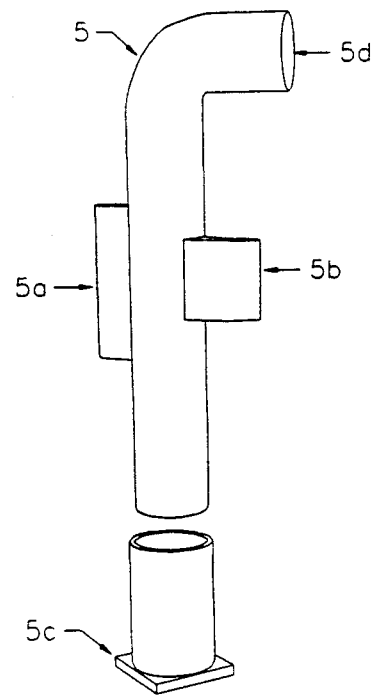
figure 8

QUICK RELEASE ADJUSTABLE DENTAL BAND CLAMP

The invention described below involves an adjustable band suited for clamping orthodontic appliances to teeth. The adjustable band is rigidly fixed to a tooth for an indefinite time period and is removable and reusable, making it different by nature from matrix bands such as in prior art U.S. Pat. No. 4,192,068. Current orthodontic bands are either handmade or preformed. Preformed bands are used more commonly since they are more time efficient; however, they require large inventories of different sizes. Another problem associated with preformed orthodontic bands is that some teeth fall in between given sizes. Preformed bands are designed to spring around any bulge on a tooth for good retention, requiring an operator to push a band over a tooth. Physically pushing on a band in the mouth is sometimes uncomfortable for a patient and the potential exists for the band pusher to slip. The invention presented would require minimal pushing and would also provide a tighter grip on a tooth and eliminate the need to pick the right size band. Preformed and hand made bands are time consuming to place and have an unsatisfactory fixated life.

The intention of this invention is to provide a more time effective and rigidly binding band. The band is made of metal, but could also be made of plastic. The band is constructed with undercut indentations (slotted) on one end which are designed to be received by a worm gear on the other end. The outer, free end of the band contains a housing for the freely rotating fixed worm. The opposite end passes under the end of the housing, through a guide. The housing guide receives the indented end and is pulled through the housing in the same direction the worm is tightened. The worm is approached from the top or superior position by a tightening tool.

There are several problems associated with hose clamping devices, such as described prior art U.S. Pat. No. 2,384,094, which make them inappropriate for use in the mouth. First, existing hose clamping devices often involve a parallel pull. However, to provide a useful band for teeth, the head of the worm must be approached from the top, perpendicular to the direction of band pull. A worm which is approached parallel to the direction of pull is more difficult to access by the physical constraints of the dental arch and teeth.

A second problem is that most hose clamping devices allow the excess band to project externally. However, the ends of the band need to be passed internally because an extending free outer end would be complicated to deal with and unacceptable in the oral cavity. Passing the free end internally was not the intent of U.S. Pat. No. 2,384,094 because it would result in too high a coefficient of friction between the hose and itself. A tooth would not offer such resistance because of its composition. Another advance is to tuck the housing free end under the slotted end by having the band material enter the housing just over the housing tab, creating no sharp free ends in the mouth. The guide then would make a curvilinear path for the band material through the housing. Another advantage to this type of path is that it would create additional compressive forces of the band material against the worm.

A third problem associated with common hose clamps is the need to screw them for placement and unscrew them for removal. A major purpose of this invention is to provide a quick release mechanism for band placement and removal. When the worm gear engages the indentations and the worm is turned as to tighten the band, stress is placed on the worm tending to cause derotation and loosening. A quick release locking pin made of a semi-flexible metal alloy or synthetic is used to prevent derotation and lock the worm into its tightened position. The locking pin has two arms. One locking pin arm engages with one gear. This arm interdigitates with the worm gear and is flexible enough to allow the worm to pass in the tightening direction. This arm is designed to grip the gears when the worm is stressed, preventing derotation. Another arm of the locking pin prevents the locking pin itself from rotating. This arm is placed in the corner of the housing. An exceptional time saver is that the clamp can be compressed with finger pressure over a tooth and then completely tightened with a hand tool. The worm can be quickly released of tension by disengaging the locking pin from the worm gears. This is accomplished by raising the locking pin in its base. The locking pin itself can be held down by a spring placed in between the top of the arms and the housing (not shown in drawings).

Another advantage provided by this invention is the slots do not go entirely through the band material. Instead, the presented invention had undercut indentations to prevent plaque accumulation and consequential demineralization of the tooth.

FIG. 4 represents a perspective of the band material.

FIG. 5 represents a perspective of the housings.

FIG. 6 represents a side view of the housing.

FIG. 7 represents an extracted view of the worm and locking pin.

FIG. 8 represents a perspective of the locking pin raised out of its base.

DRAWINGS

Figure 1:
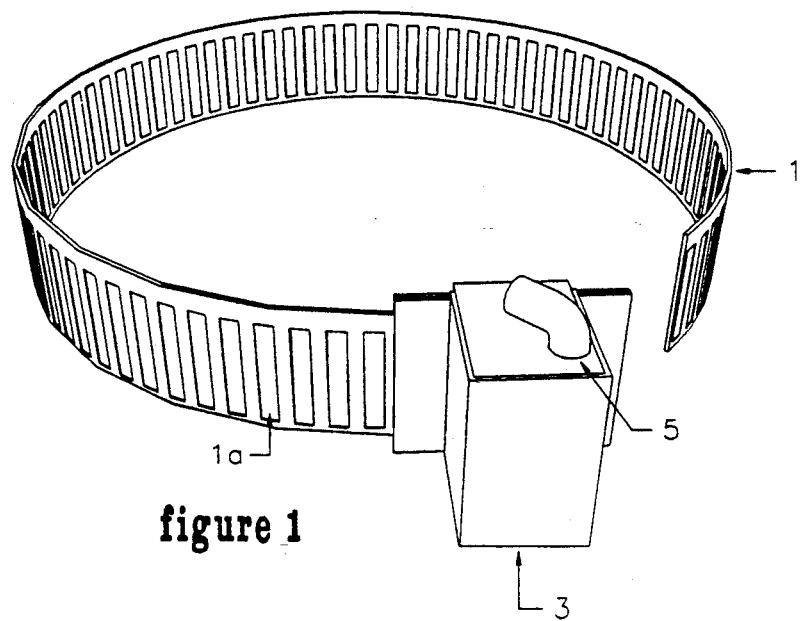
FIG. 1 represents a perspective view.
Figure 2:
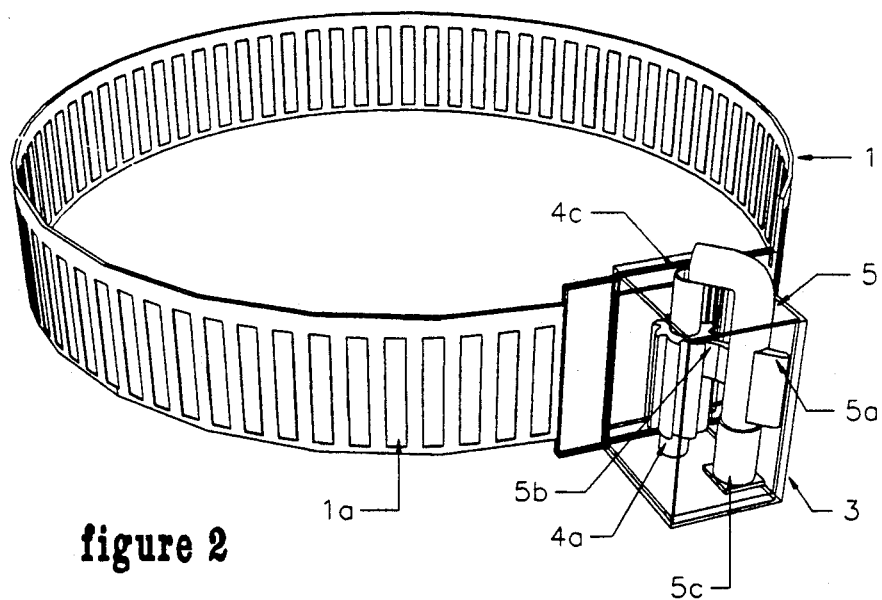
FIG. 2 represents a perspective view with transparent housing.

FIGS. 1 and 2 are perspective views of an adjustable band with quick release. FIGS. 1 and 2 show a band (1) with indented slots (1a), a housing unit (3) containing a free-spinning, rigidly held worm (4) and a quick release locking pin (5).

FIG. 2 shows a transparent housing (3) revealing the interdigitation of the parts of this invention. The worm (4) has worm gear (4a) to engage indentation slots (1a). The band (1) will decrease in diameter as an operator tool fits into wrench hole (4b) and turns in the closing direction. The worm (4) is kept from spinning freely by a locking pin (5). One lock pin arm (5b) interdigitates with the worm gear (4a) to allow turning in the tightening direction, but not in the loosening direction. The other locking pin arm (5a) prevent backspin rotation from occurring. The lock pin (5) is held in place by a fixed base (5c).

Figure 3:
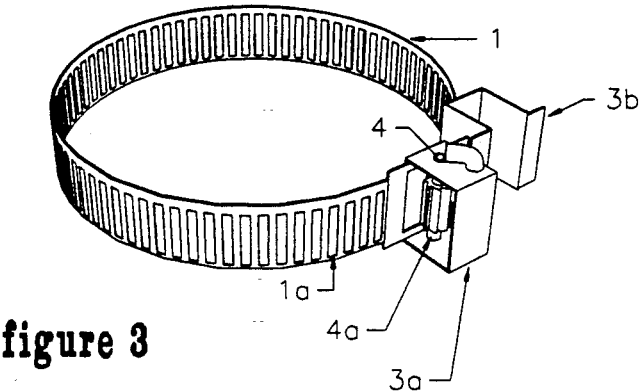
FIG. 3 represents a perspective view with the housing partially unfolded.

FIG. 3 shows the partial assembly of the invention. Housing (3) unfolds in two halves (3a and 3b) and is made of stamped out sheet metal. One half (3a) is designed to hold the worm and locking pin in place. The other half (3b) is partially unfolded and is designed to form a complete encasement. Hole (2a) is designed to receive the locking pin.

FIG. 4 presents the band (1) alone, revealing its tab (1B) to which the housing (3) is spot welded. The tab (1b) contains a cutout section (1c) which the worm gears pass through before they engage the indentations (1a).

FIG. 5 is a perspective view of the housing (3). The housing tab (3c) is designed to be spot welded to the band tab (1B) as shown in FIGS. 1 through 3. The locking pin and worm are to pass through the housing (3) through two holes (2a and 2 b, respectively).

FIG. 6 is a side view of the housing (3), revealing the guide plate (3d) and the band receiving space (3e). The band receiving space (3e) is approximately the thickness of two bands. In assembly, the band tab (1b) fits into the band receiving space (3e) and is spot welded to the housing tab (3c). The free end of the band (1) enters through guide entering port (3f) and exits on the other side of the housing between the band tab (1b) and the housing guide plate (3d).

FIG. 7 shows the worm gear (4) and the locking pin (5), demonstrating their operational mechanics. When the worm (4) is cranked by an operator tool (not shown), the locking pin arm (5b) allows the worm to pass decreasing band circumference and prevents circumferential increase while in the lock position. The other locking pin arm (5a) is placed in the corner of the housing (3) to stabilize its position.

FIG. 8 shows how the quick release locking pin (5) is lifted out of its base (5c). This motion would disengage the locking pin arm (5b) from the worm gear (4a) to allow free spinning of the worm and therefore increases in circumference.

I claim:

1. A quick release adjustable band clamp with a mechanism for a circumferential tightening of band material, with slots on one underlapping end that provide a grip for a worm on one overlapping end to form a central hole, whereby said worm is perpendicularly placed in a housing parallel with said hole's central axis and the worm gear engages and draws said band material's slotted end through a guide such that said guide enforces the biting engagement of one said worm gear to one said slot, and with a movable locking pine means including one perpendicularly placed in said housing, parallel to said worm, with an extension arm to engage one said worm gear in one position and capable of movement to disengage said locking pin arm from said worm, said guide includes a curvilinear guide which initially directs said undercut slotted end over said housing's free end to make said curvilinear path inside said housing providing additional pressure on said worm and to pass out of said housing towards said hole's interior, whereby no free end of said band material projects externally, said locking pin is held in said housing via a fixed base sleeve and passes through the top of said housing, where said locking pin can be manually manipulated.

2. A quick release adjustable band clamp as in claim 1 wherein said slots are undercut indentations.

3. A quick release adjustable band clamp as in claim 1 wherein said worm is made of a rigid nonflexible material, including hardened steel.

4. A quick release adjustable band clamp as in claim 1 in which said worm is freely turned in the tightening direction by an operator and prevented from otherwise loosening via a moveable locking mechanism which has an extension arm to engage with one said worm gear and function in the following manner:
  1) Flexibly allow said worm to pass in the tightening direction
  2) Rigidly resist said worm from passing in the loosening direction while engaged.

5. A quick release adjustable band clamp as in claim 1 wherein said locking pin contains a means that prevents twisting in said housing while engaged with said worm and includes an arm placed in the corner of said housing allowing only up and down movement of said locking pin.

6. A quick release adjustable band clamp as in claim 1 wherein an operator can disengage said locking pin from said worm allowing said worm to freely turn, thereby permitting easy removal.

* * * * *